United States Patent [19]
Murazumi

[11] Patent Number: 5,399,006
[45] Date of Patent: Mar. 21, 1995

[54] MULTI-STAGE STORAGE CASE FOR CASSETTES OR CASSETTES BLOCKS

[75] Inventor: Takuya Murazumi, Ashiya, Japan

[73] Assignee: Murazumi Industrial Co., Ltd, Himeji, Japan

[21] Appl. No.: 290,120

[22] Filed: Aug. 15, 1994

Related U.S. Application Data

[63] Continuation of Ser. No. 957,867, Oct. 8, 1992, abandoned.

Foreign Application Priority Data

Oct. 11, 1991 [JP] Japan .................. 3-091433 U

[51] Int. Cl.⁶ .............................................. A47B 88/00
[52] U.S. Cl. ............................ 312/109; 312/9.53
[58] Field of Search .................. 312/109, 9.48, 9.53, 312/9.56, 330.1, 334.44, 334.46, 384

[56] References Cited

U.S. PATENT DOCUMENTS

| | | | |
|---|---|---|---|
| 1,774,237 | 8/1930 | Rand, Jr. | 312/109 X |
| 3,722,975 | 3/1973 | Taylor | 312/334.44 X |
| 3,918,781 | 11/1975 | Paris | 312/334.44 X |

Primary Examiner—Timothy V. Eley
Assistant Examiner—Khan V. Nguyen
Attorney, Agent, or Firm—Armstrong, Westerman, Hattori, McLeland & Naughton

[57] ABSTRACT

A plurality of U-sectioned shelf units 14 are disconnectably mounted one upon another between a base unit 12 and a top unit 13, each drawer 15 for accommodating cassettes or cassette blocks 16 is inserted into each shelf unit 14, freely slidable and a projection 45 is formed on the upper edge of the rear wall 41 of the drawer 15 which disengageably engage with the indented stoppers 31 provided in the underside of the top unit 13 and each shelf unit 14 so that the drawer 15 can be pulled out stepwise because of the projection 45 being engaged with the indented stopper 31. It is convenient since the number of shelf units 14 disconnectably connected is adjustable as necessary. Also, the drawer 15 can be pulled out stepwise being stopped at any of the stoppers provided in the shelf unit, hence the drawer 15 pulled out halfway is ensured against further sliding out of the shelf unit.

11 Claims, 9 Drawing Sheets

PRIOR ART

FIG. 10
PRIOR ART

MULTI-STAGE STORAGE CASE FOR CASSETTES OR CASSETTES BLOCKS

This application is a continuation of application Ser. No. 07/957,867, filed Oct. 8, 1992, now abandoned.

BACKGROUND OF THE INVENTION

1. Field of the Invention

The present invention relates to a multi-stage storage case for cassettes for specimens for histopathological examination, or for sorting, storing or transporting cassette blocks made by setting the aforementioned specimen in the cassette using paraffin before or after cutting into slices for microscopic examination.

2. Description of the Prior Art

Figure 9:
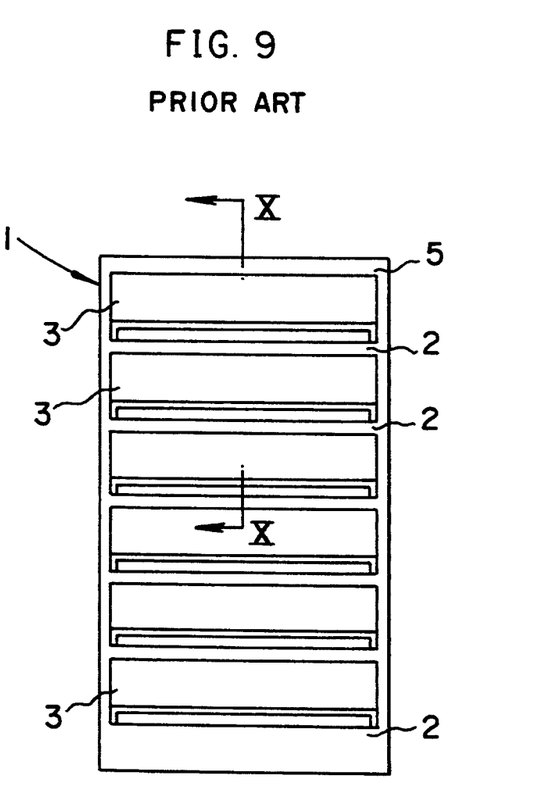
FIG. 9 is a front view of an example of conventional multi-stage storage case for cassettes or cassette blocks.
Figure 10:
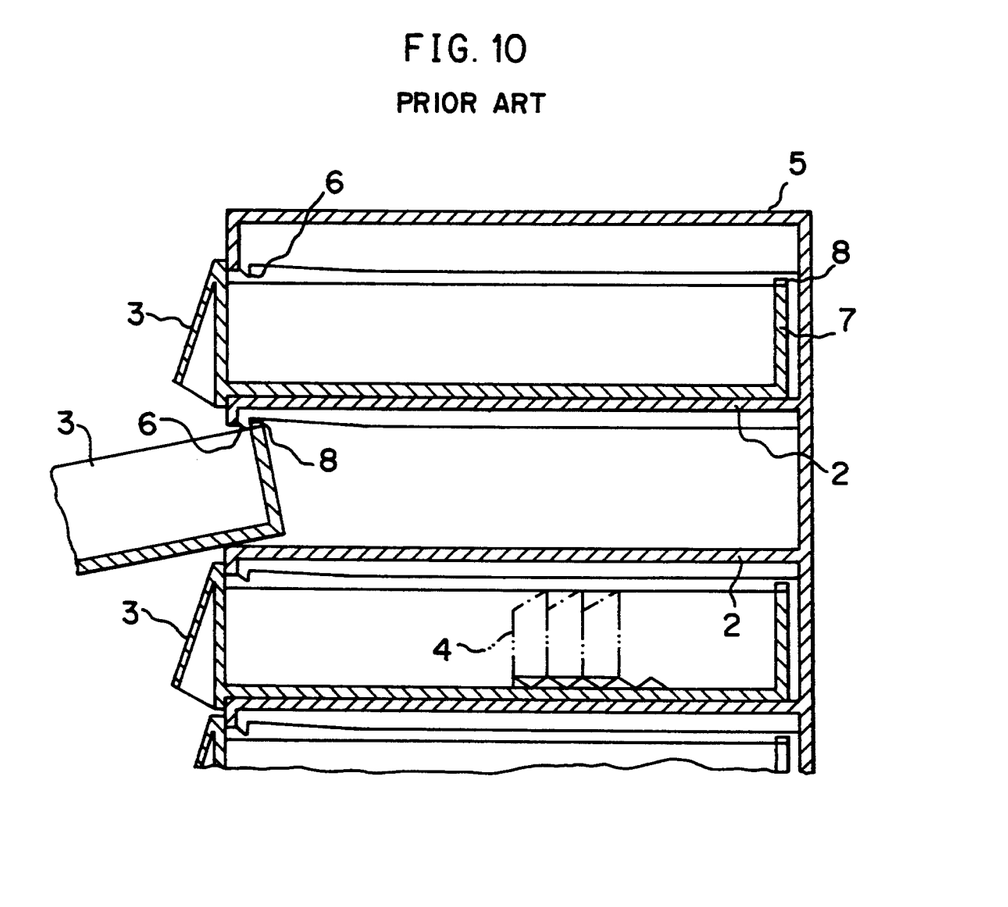
FIG. 10 is a sectional view taken along the line X—X of FIG. 9.

Hitherto, this kind of multi-stage storage case was made of a synthetic resin such as ABS resin and, as seen from FIGS. 9 and 10, its construction was such that the case housing 1 was made of a plurality (usually 6) of shelf units 2 and each shelf unit 2 has housed therein freely slidably a drawer 3, in which cassettes (or cassette blocks) 4 were stored. A pair of (left and right) indented stoppers 6 were formed under the front edge portion of a top unit 5 and shelf units 2, the rear wall 7 of each drawer 3 has formed thereon a pair of (left and right) projections 8 engageably with and disengageably from the indented stoppers 6 so as to ensure against sliding out of the drawer 3 (See FIG. 10.).

With a conventional multi-stage storage case as described above, there was an inconvenience of necessarily using one whole case even for transportation of a small number of cassettes 4 for which one or two drawers 3 suffices. Another problem was that when it suffices to pull out drawers 3 only partly to take in or take out the wanted number of cassettes 4, the drawer 3 partly pulled out inclined with the front end down, this resulting in spontaneous sliding of the drawer with its own weight and that of the cassettes 4 therein and possibly sliding completely out of the case to drop because of the disconnection of the projections 8 from the indented stoppers 6.

SUMMARY OF THE INVENTION

The object of the present invention is, therefore, to eliminate such defects through improvement of the conventional multi-stage storage case as mentioned above.

Other objects and advantages of the present invention will be apparent to those skilled in the art from the following detailed description.

In order to accomplish the aforementioned object, the multi-stage storage case of the present invention is characterized in that a plurality of U-sectioned shelf units are connected one upon another disconnectably between a base unit and a top unit one upon another, a drawer for cassettes or cassette blocks is slidably put in each shelf unit, a plurality of indented stoppers are formed longitudinally in the underside of said top unit and each shelf unit, an upward projection is provided on top of the rear wall of said drawer disengageably engaged with said indented stoppers and said drawers can be pulled out with said upward projections engaged with said indented stoppers.

It is preferred to provide recesses in the front edge portion of the topside of each shelf unit for locking the drawer and also provide indented stoppers on the front edge portion of the underside of the drawer, the aforementioned indented stoppers being engageable with and disengageable from the aforementioned recesses so as to enable locking of the drawer in the closed state.

It is also possible to provide a continuous indentation in the topside of the bottom plate of the drawer for preventing sliding of cassettes or cassette blocks.

DETAILED DESCRIPTION OF THE INVENTION

An embodiment of the present invention will be described below in detail with reference to FIGS. 1-8.

Figure 1:
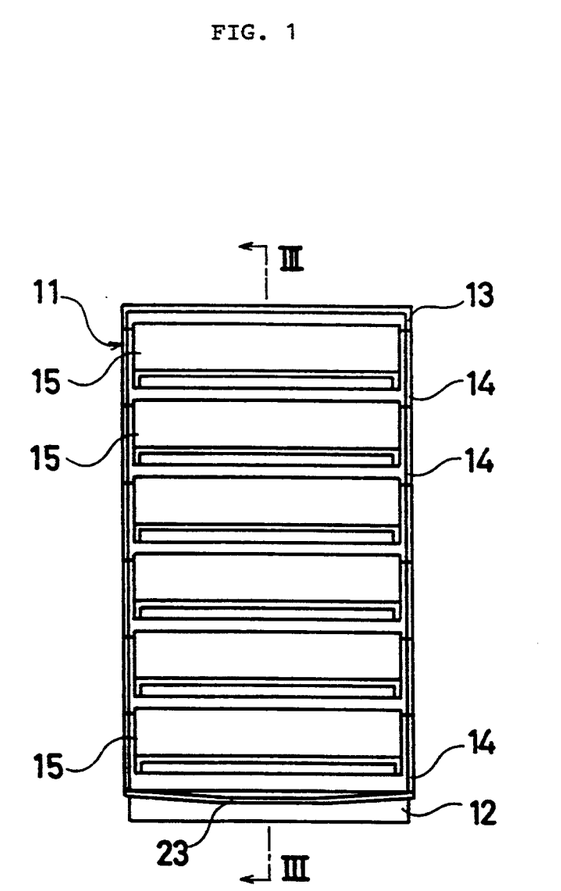
FIG. 1 is a front view of a multi-stage storage case for cassettes or cassette blocks showing an embodiment of the present invention.
Figure 2:
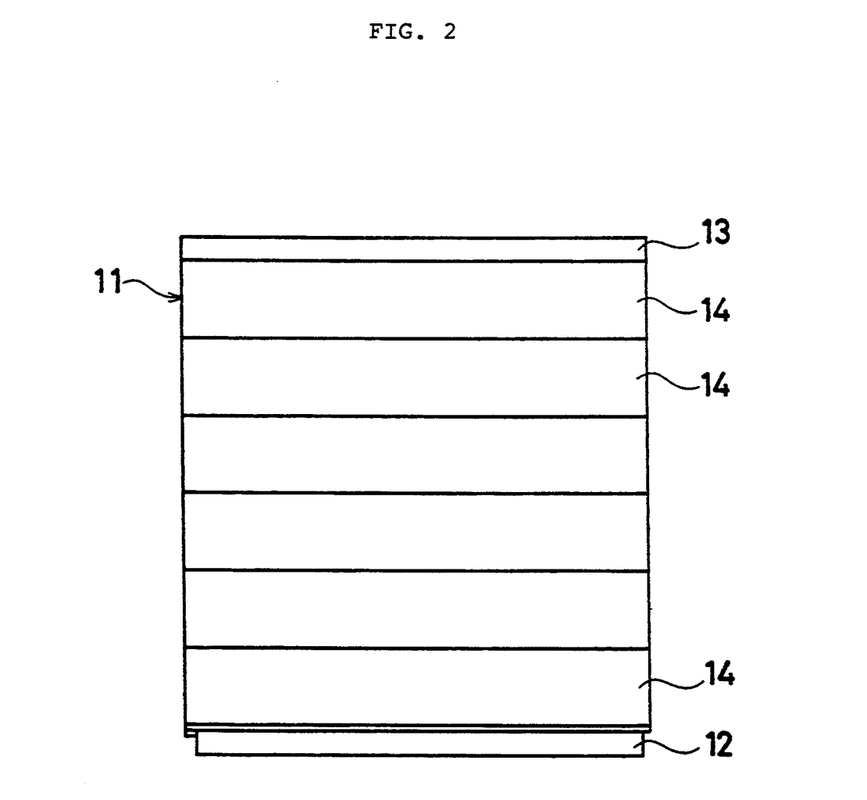
FIG. 2 is a left side view of the embodiment shown in FIG. 1

The multi-stage case for storage of cassettes or cassette blocks (hereinafter called cassettes) are, as shown in FIGS. 1 and 2, in which a case housing 11 is made up of a plurality (6 in the illustrated case) of shelf units 14 connected one upon another, between a base unit 12 and a top unit 13, each shelf unit 14 including a drawer 15 and in each drawer 15 a plurality of cassettes 16 are arranged erect (See the lowermost drawer shown in FIG. 3). The base unit 12, the top unit 13, the shelf units 14 and the drawers 15 are all integrated molding of synthetic resins such as an ABS resin.

Figure 3:
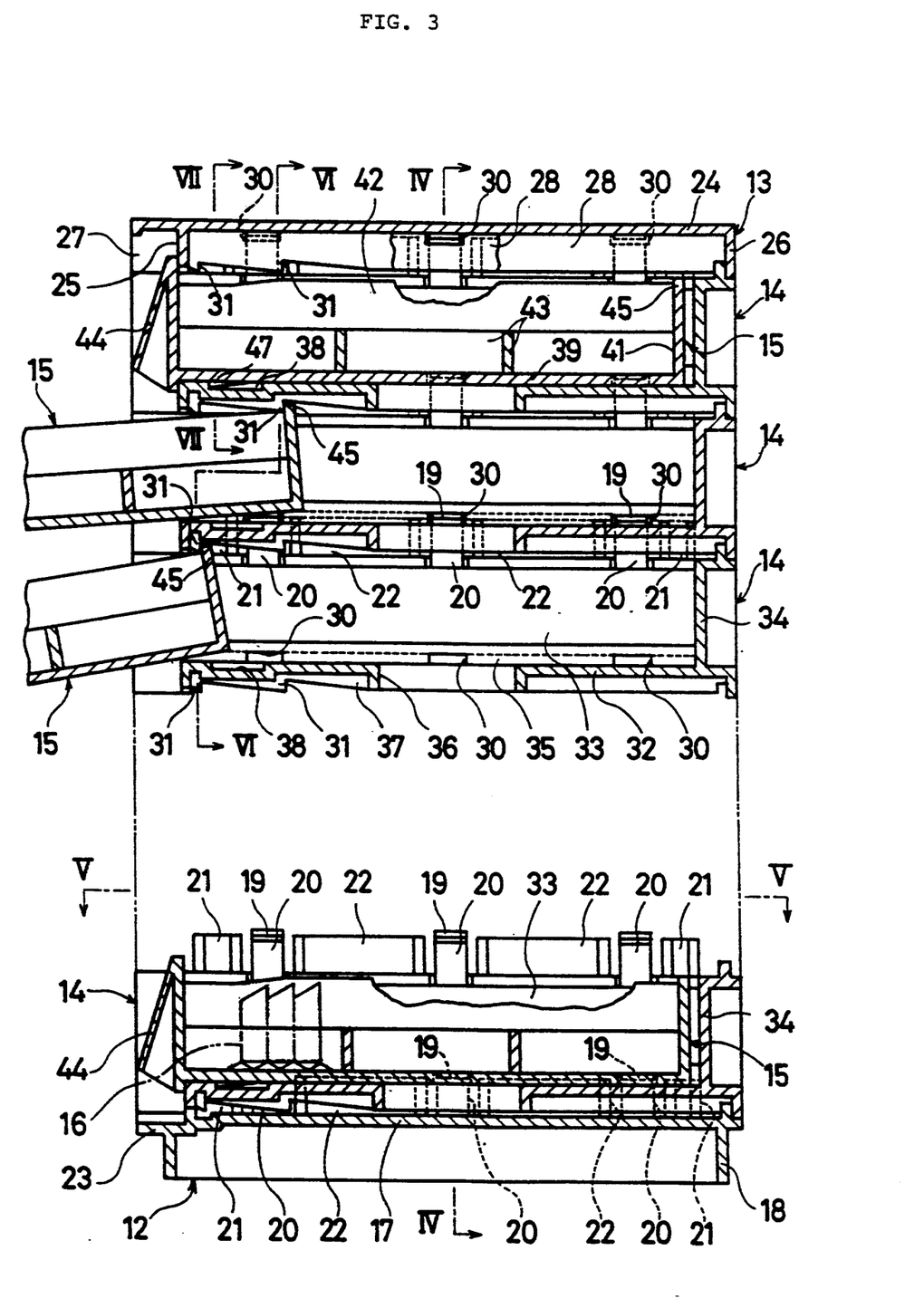
FIG. 3 is a sectional view taken along the line III—III of the embodiment shown in FIG. 1 with part thereof omitted.
Figure 4:
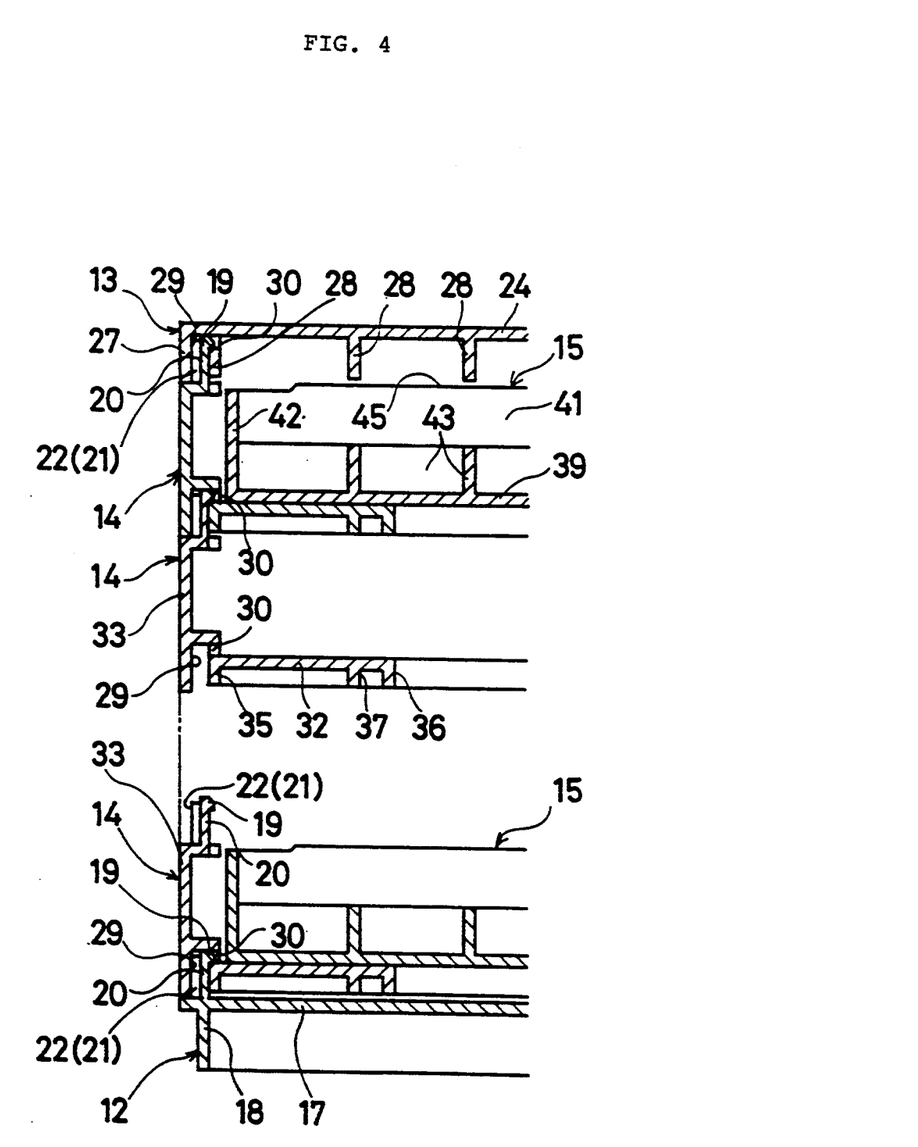
FIG. 4 is a sectional view taken along the line IV—IV of the embodiment shown in FIG. 1 with part thereof omitted.

As shown in FIGS. 3 and 4, the base unit 12 is made up of a bottom plate 17 and legs 18 extending downward from each side of the bottom plate 17. On both (left and right) sides of the topside of the bottom plate 17, there are provided 3 pairs of stopping walls 20 having indented stoppers 19 at the front ends thereof and 4 pairs of guide walls 21, 22 are arranged erect alternately and longitudinally. The front edge of the bottom plate 17 is curved downward in an arc shape to facilitate applying fingers to the inside of a handle 44 of the drawer 15 at the lowermost in pulling out the drawer (See FIG. 1.).

As seen from FIGS. 3 and 4, the top unit 13 is made up of a top plate 24, a front wall 25, a rear wall 26 and side walls 27 extending downward from edges of the top plate and six longitudinal ribs 28 formed in parallel downward from the underside thereof. Of these ribs 28, as seen from FIG. 4, the two (left and right) longitudinal ribs 28 have guide grooves 29 formed between them and the side walls 27 and, as seen from FIGS. 3 and 4, and each has three square holes 30. The four inside longitudinal ribs 28, as seen from FIGS. 3 and 6, have a plurality (two in the illustrated case) of indented stoppers 31 at the lower front ends and between the front and rear ends.

Figure 6:
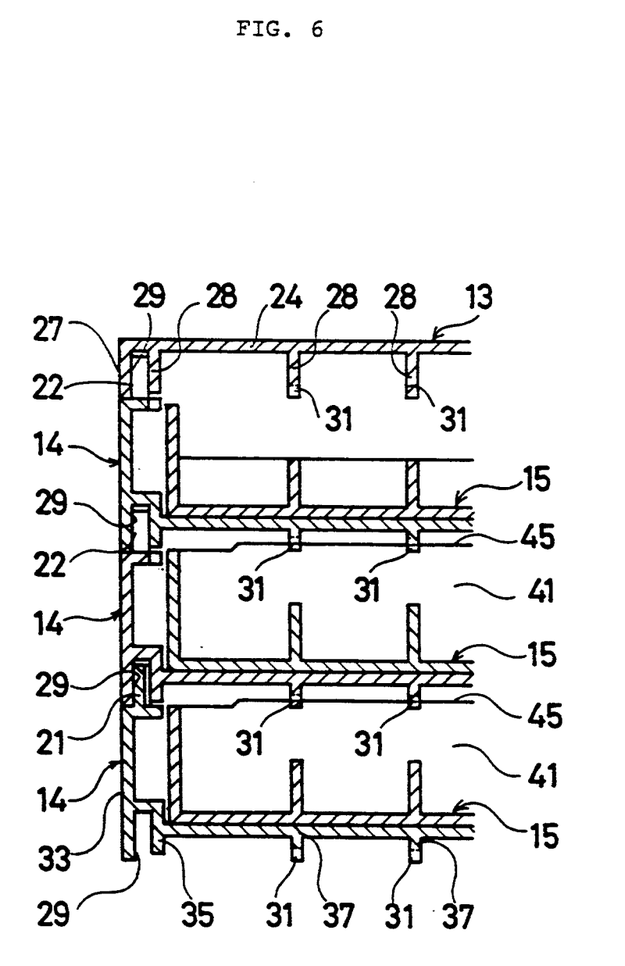
FIG. 6 is a sectional view taken along the line VI—VI of FIG. 3.
Figure 7:
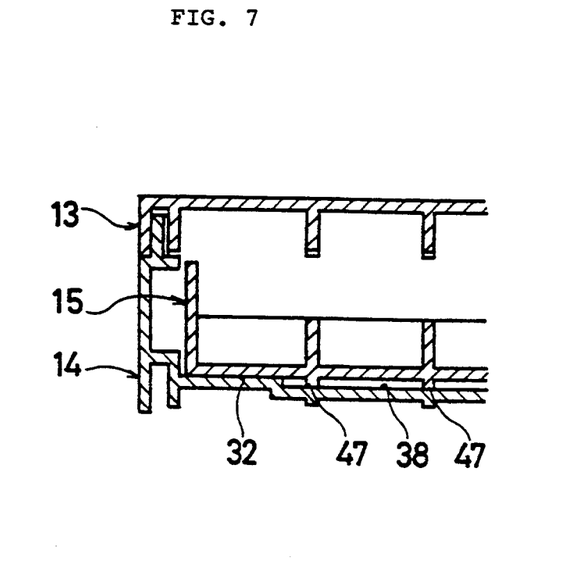
FIG. 7 is a sectional view taken along the line VII—VII of FIG. 3.

As seen from FIGS. 3 and 4, the shelf unit 14 has U-shaped cross-section and is made up of a shelf board 32 having inverse L-sectioned (left and right) side walls 33 and a rear wall 34. The shelf board 32 is, as seen from FIGS. 3 and 4, connected with the side walls 33 via drawer guides 35, has access holes 36 about the center for disconnecting the shelf units, has four longitudinal, parallel ribs 37 formed on its underside, as shown in FIGS. 3 and 6, and on both (left and right) sides of the front end of the topside there are provided recesses 38 for locking the drawer 15, as shown in FIGS. 3 and 7.

Figure 5:
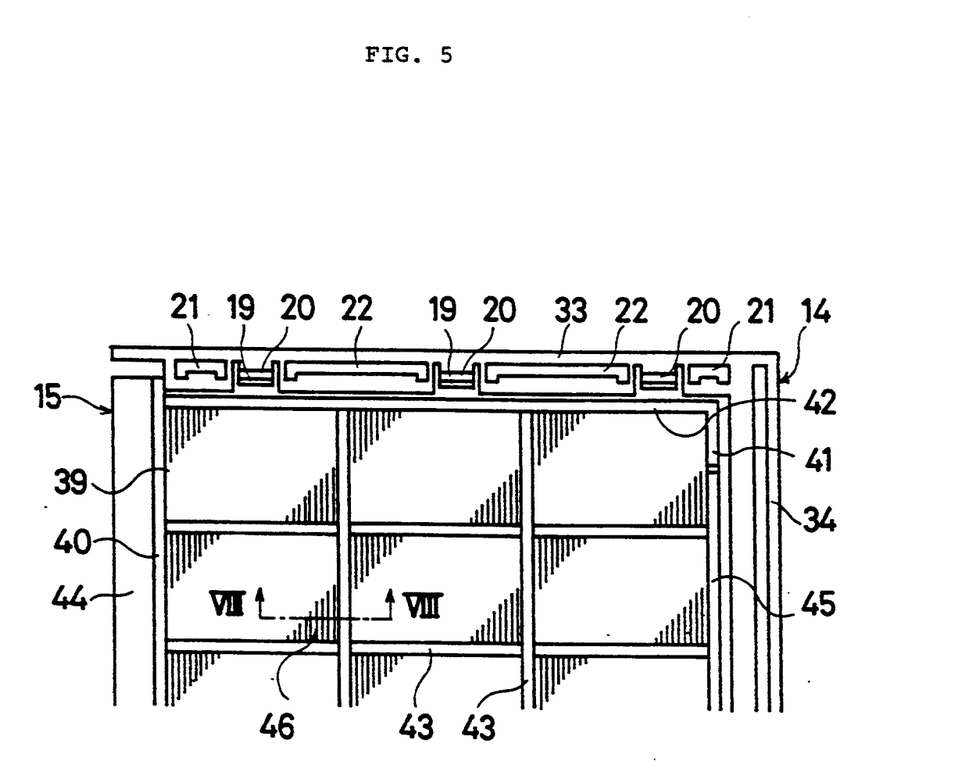
FIG. 5 is an arrow view taken along the line V—V of FIG. 3.

The drawer guide 35, like the longitudinal ribs 28 on both (left and right) sides of the aforementioned top unit 13, forms guide grooves 29 between it and the side walls 33, there are provided square holes 30 at three longitudinal positions and the longitudinal ribs 37, like the central (inside) longitudinal ribs 28 extending downward from the aforementioned top unit 13, has indented stoppers 31 at the lower front edge and a plurality (two in the illustrate case) of points between the front and rear ends. On the topside of the side (left and right) walls 33, as shown in FIGS. 3–5, there are provided, as in the aforementioned base unit 12, three pairs of stopping walls 20 with indented stoppers 19 formed at the front end thereof and four pairs of guide walls 21, 22 arranged longitudinally and alternately. The base of the stopping walls 20 is formed by cutting off part of the side walls 33 in order to increase the elasticity of the stopping wall 20 (See FIG. 5.). The indented stoppers 19 of the stopping walls 20 formed erect on the base unit 12 and the shelf unit 14 are made freely engageable with and disengageable from the square holes 30 made in the shelf unit 14 or the top unit 12 placed immediately above by the elasticity of the stopping wall 20.

Figure 8:
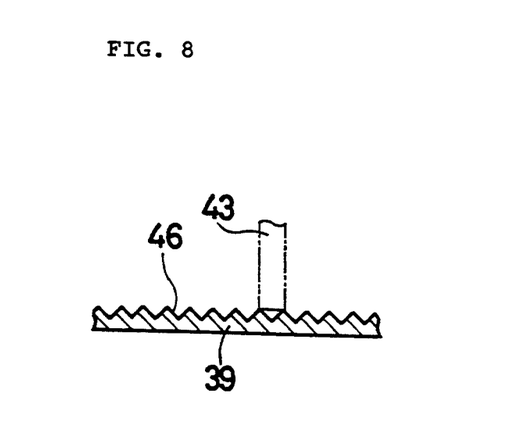
FIG. 8 is a sectional view taken along the line VIII—VIII of FIG. 5.

As seen from FIGS. 3–5, the drawer 15 is made up of a front wall 40, rear wall 41 and side (left and right) walls 42 extending erect from the bottom plate 39 and its interior is partitioned by partitions 43 into a plurality of spaces. A handle is formed before the front wall 40 and on the upper edge of the rear wall 41 there is formed a projection 45 as shown in FIG. 4. This projection 45 is formed freely engageable with and disengageable from the indented stopper 31 provided in the underside of shelf unit 14 or the top unit 13 placed immediately above. The bottom plate 39 has in its topside, as shown in FIGS. 5 and 8, a continuous longitudinal indentation 46 extending laterally to ensure against sliding of cassettes and also has in the front portion of the underside a plurality (4 in the illustrated case) of indented stoppers 47 as shown in FIGS. 3 and 7. These indented stoppers 47 are formed freely engageable with and disengageable from the drawer locking recesses 38 provided in the shelf unit 14 corresponding to the drawer 15.

The cassettes 16, when they are stored in the drawer 15 erect, as shown in FIG. 3, the necessary matters such as name and date can be written on the top side thereof.

In assembling the multi-stage storage case of the construction as described above, first, as shown in FIGS. 3, 4 and 6, the case housing 11 is assembled by first putting between the base unit 12 and the top unit 13 a plurality of shelf units 14 and then the stopping walls 20 and guide walls 21, 22 of the base unit 12 and each shelf unit 14 are inserted into the guide grooves 29 formed in the underside of the shelf unit 14 or the top unit 13 immediately above and have each indented stopper 19 of each stopping wall 20 engaged in each square hole 30. Then, the drawer 15 is inserted into each shelf unit 14 with the handle 44 lifted up a little. The projection 45 of the rear wall 41 of the drawer 15 passes under indented stoppers 31 formed in the shelf unit 14 or the top unit 13 immediately above and, as shown in FIGS. 3 and 7, the indented stoppers 47 of the drawer 15 are engaged with the recesses 38 for locking of the shelf unit 14 and the drawer 15 is locked thereby.

In order to put the cassettes 16 into the drawer 15 of the multi-stage storage case thus assembled, first the handle 44 of the drawer 15 is lifted a little to disengage the recess 38 for locking the drawer 15 from the indented stopper 47 of the drawer 15, and then the drawer 15 is pulled out halfway (or entirely, if necessary). As shown in FIGS. 3 and 6, the drawer 15 inclines through its own weight the front end down, the projection 45 of the rear wall 41 engages the indented stoppers 31 of the shelf unit 14 immediately above or the top unit 13 to ensure against further sliding out of the shelf unit 14. The cassettes 16 are, as shown in FIG. 3, stored in the drawer arranged erect, with the side in which the referring index is written facing up, to make it easily visible and the drawer is then pushed in. The procedure is essentially the same when the cassettes are taken out of the drawer 15. The indentations 46 (See FIG. 8.) formed in the topside of the bottom plate 39 of the drawer 15 are for ensuring against sliding or falling of the cassettes 16 as the drawer 15 is pulled out or pushed in.

In disassembling the storage case into the base unit 12, the top unit 13 and and shelf units 14, all or part of the drawers 15 are pulled out, and then, with a hand inserted through the front opening of the shelf unit 14 and working with fingers through the access hole 36 to disengage the indented stoppers 19 of the stopping walls 20 of the base unit 12 or the shelf unit 14 from the square holes 30 in the shelf unit 14 or the top unit 13 for separation of the base unit 12, the top unit 13 or each shelf unit 14. It is thus possible to adjust the number of the shelf units 14 according to the number of cassettes 16 to be stored or disassemble a multi-stage storage case as a whole.

Although in this embodiment the depth of each drawer 15 was made uniform but in other embodiments drawers different in depth can be used in combination so as to enable an increase of the kinds of cassettes that can be stored in a single storage case.

Since, as described above, the present invention consists in putting a plurality of shelf units one upon another separably between the base unit and the top unit, the number of shelf units can be adjusted according to the number of cassettes or cassette blocks to be stored and, moreover, it is possible to use drawers different in depth in combination in a single storage case, this resulting in improved transporting and/or storing efficiency.

Also, since the drawer can be pulled out stepwise with the projection formed on the upper edge of its rear wall engaged with a plurality of the indented stoppers provided in the top unit and each shelf unit immediately above, workability is improved with simultaneous increase of the drawer's holding capability to ensure against spontaneous sliding out of the drawer pulled out halfway.

It is also possible to prevent spontaneous sliding of drawers out of the case due to inclination of storage case since each drawer is locked in the closed state with the indented stopper provided in the drawer engaged with the locking recess provided in the shelf unit.

Further, by providing anti-sliding indentation in the topside of the bottom plate of the drawer it is possible to ensure against sliding or falling of cassettes or cassette blocks arranged erect in the drawer as it is pulled out or pushed in.

What is claimed is:

1. A multi-stage storage case for cassettes or cassette blocks, comprising:
    a base unit;
    a top unit;
    a plurality of U-sectioned shelf units connectable one upon another between said base unit and said top unit;
    a plurality of drawers for cassettes or cassette blocks, each of said drawers being transversely slidable in a respective shelf unit in a longitudinal direction extending from a front side to a rear side of said drawer;
    a plurality of indented stoppers formed in the underside of each of said top unit and said shelf units, each said plurality of stoppers being displaced in said longitudinal direction such as to create a plurality of stopping locations, at least one of said stopping locations being located to provide a halfway open position of the drawer providing access to a portion of the cassette space within the drawer and one of said stopping locations being located to provide an entirely open position providing full access to the cassette space within the drawer;
    an upward projection provided on top of a rear wall of each said drawer which is disengageably engageable with a respective one of said plurality of indented stoppers;
    wherein when each said drawer is pulled out from the respective shelf unit, said upward projection engages respectively with each of said plurality of indented stoppers so as to create a plurality of positions of said drawer corresponding to each of said stopping locations; and
    wherein said shelf units include a shelf board for supporting a drawer thereon, said shelf board including a plurality of parallel ribs extending in said longitudinal direction on a lower surface thereof, said indented stoppers being formed in said parallel ribs.

2. The multi-stage storage case according to claim 1, wherein recesses for locking each drawer are provided in an upper front edge portion of each shelf unit, and wherein a stopper is provided in the lower front edge portion of each drawer engageable with and disengageable from a respective one of said recesses to thereby lock said drawer in a closed position in the respective shelf unit.

3. The multi-stage storage case according to claim 1 or 2, wherein a continuous indentation is formed in the topside of a bottom plate of each said drawer to ensure against sliding of the cassettes or cassette blocks.

4. The multi-stage storage case according to claim 1, wherein each of said shelf units has two opposing side walls and a rear wall, each of said side walls having at least one resilient stopping wall extending at an upper portion thereof and situated inward from an outer surface of the respective side wall, said resilient stopping wall being engageable with a shelf unit placed there-above, the shelf unit placed there-above engaging with the lower shelf unit in such a manner that the side walls of the shelf units extend over the engagement of the respective stopping wall such that said engagement is not visible from the sides of the storage case.

5. The multi-stage storage case according the claim 4, wherein said stopping walls engage within drawer guides extending inside the shelf unit there-above, said drawer guides being located between said side walls of each shelf unit and a bottom wall of each shelf unit on both sides of the shelf unit, and said drawer guides extending above the height of the bottom wall.

6. The multi-stage storage case according to claim 4, wherein said shelf units include a lower shelf board having an access opening in the center thereof enabling access therethrough by an individual for disassembly of the storage case.

7. The multi-stage storage case according to claim 1, wherein said indented stoppers are each formed from a gradually inclined surface of the ribs adjacent a generally vertical stopping surface of the rib, and wherein there are two of such indented stoppers.

8. The multi-stage storage case according to claim 7, wherein said drawer is capable of being moved past said indented stoppers by lifting a forward portion of the drawer slightly in order to disengage the upward projection from the respective indented stopper.

9. The multi-stage storage case according to claim 2, wherein said stopper on the lower front edge of each drawer includes an inclined surface towards the rear of the drawer so as to facilitate placement of the drawer within the respective shelf unit.

10. The multi-stage storage case according to claim 9, wherein said stopper is disengageable from said recess in the respective shelf unit by lifting a forward edge of the drawer so as to lift said stopper to a position free from engagement with the respective recess.

11. A multi-stage storage case for cassettes or cassette blocks, comprising:
    a base unit;
    a top unit;
    a plurality of U-sectioned shelf units connectable one upon another between said base unit and said top unit;
    a plurality of drawers for cassettes or cassette blocks, each of said drawers being transversely slidable in a respective shelf unit in a longitudinal direction extending from a front side to a rear side of said drawer;
    a plurality of indented stoppers formed in the underside of each of said top unit and said shelf units, each said plurality of stoppers being displaced in said longitudinal direction such as to create a plurality of stopping locations, at least said one of stopping locations being located to provide a halfway open position of the drawer providing access to a portion of the cassette space within the drawer and one of said stopping locations being located to provide an entirely open position providing full access to the cassette space within the drawer;
    an upward projection provided on top of a rear wall of each said drawer which is disengageably engageable with a respective one of said plurality of indented stoppers;
    wherein when each said drawer is pulled out from the respective shelf unit, said upward projection engages respectively with each of said plurality of indented stoppers so as to create a plurality of positions of said drawer corresponding to each of said stopping locations;

wherein said shelf units include a shelf board for supporting a drawer thereon, said shelf board including a plurality of parallel ribs extending in said longitudinal direction on a lower surface thereof, said indented stoppers being formed in said parallel ribs;

wherein said shelf units include a shelf board for supporting a drawer thereon, said shelf board including a plurality of parallel ribs extending in said longitudinal direction on a lower surface thereof, said indented stoppers being formed in said parallel ribs;

wherein said indented stoppers are each formed from a gradually inclined surface of the ribs adjacent a generally vertical stopping surface of the rib, and two indented stoppers are on each of said ribs; and wherein said indented stoppers on adjacent ribs are, respectively, aligned in a transverse direction, with each stopping location being defined by engaging the upward projection with the respectively aligned stoppers.

* * * * *